US012635897B2

(12) United States Patent
Kioka et al.

(10) Patent No.: US 12,635,897 B2
(45) Date of Patent: May 26, 2026

(54) EVALUATION METHOD, PROGRAM, AND EVALUATION SYSTEM

(71) Applicant: OSAKA UNIVERSITY, Osaka (JP)

(72) Inventors: Hidetaka Kioka, Suita (JP); Yusuke Takahashi, Suita (JP); Shinichiro Fukuhara, Suita (JP); Yasushi Sakata, Suita (JP); Norio Nonomura, Suita (JP); Seiji Takashima, Suita (JP); Shigeyoshi Saito, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 209 days.

(21) Appl. No.: 18/265,040

(22) PCT Filed: Nov. 25, 2021

(86) PCT No.: PCT/JP2021/044174
§ 371 (c)(1),
(2) Date: Jun. 2, 2023

(87) PCT Pub. No.: WO2022/118906
PCT Pub. Date: Jun. 9, 2022

(65) Prior Publication Data
US 2024/0008761 A1 Jan. 11, 2024

(30) Foreign Application Priority Data

Dec. 4, 2020 (JP) ................................. 2020-201814

(51) Int. Cl.
*A61B 5/055* (2006.01)
*A61B 5/00* (2006.01)
*G01R 33/485* (2006.01)
(52) U.S. Cl.
CPC ............ *A61B 5/055* (2013.01); *A61B 5/4387* (2013.01); *G01R 33/485* (2013.01)

(58) Field of Classification Search
CPC .... A61B 5/055; A61B 5/4387; G01R 33/485; G01R 33/5605; G01R 33/5608
See application file for complete search history.

(56) References Cited

U.S. PATENT DOCUMENTS

2012/0108944 A1 5/2012 Turek et al.

FOREIGN PATENT DOCUMENTS

| JP | 2012-524628 | 10/2012 |
| JP | 2015-156894 | 9/2015 |
| JP | 2016-174656 | 10/2016 |

OTHER PUBLICATIONS

English language translation of International Preliminary Report on Patentability issued May 30, 2023 in corresponding International (PCT) Patent Application No. PCT/JP2021/044174.
(Continued)

*Primary Examiner* — Amelie R Davis
(74) *Attorney, Agent, or Firm* — Wenderoth, Lind & Ponack, L.L.P.

(57) ABSTRACT

An evaluation method is performed by an arithmetic circuit and includes obtainment processing (S1), evaluation processing (S2), and presentation processing (S3). The obtainment processing (S1) obtains: image information on a sectional image representing an interested section of an organism including a target section of a testis of the organism generated by use of magnetic resonance of hydrogen atoms; and concentration information on a creatine concentration in the interested section measured by use of magnetic resonance based on chemical exchange saturation transfer. The evaluation processing (S2) generates an evaluation image representing a distribution of evaluation results of a testicular function in the target section based on the concentration information. The presentation processing (S3) presents the sectional image and the evaluation image.

13 Claims, 12 Drawing Sheets

(56)               References Cited

OTHER PUBLICATIONS

International Search Report issued Mar. 8, 2022 in International (PCT) Application No. PCT/JP2021/044174.

Storey, Pippa et al., "Quantitative proton spectroscopy of the testes at 3 tesla: towards a noninvasive biomarker of spermatogenesis", Invest. Raidol., 2019, vol. 53, No. 2, pp. 87-95.

Kogan, Feliks et al., "Method for High-Resolution Imaging of Creatine in Vivo Using Chemical Exchange Saturation Transfer", Magnetic Resonance in Medicine, 2014, vol. 71, No. 1, pp. 164-172.

Extended European Search Report issued Apr. 15, 2024 in European Patent Application No. 21900657.4.

Pippa Storey et al., "Quantitative proton spectroscopy of the testes at 3 testes at 3 T: Towards a noninvasive biomarker of spermatogenesis", Invest Radiology, Feb. 1, 2018, vol. 53, No. 2, pp. 1-23.

Dong-Hoon Lee et al: "In VivoMapping and Quantification of Creatine Using Chemical Exchange Saturation Transfer Imaging in Rat Models of Epileptic Seizure", Molecular Imaging & Biology, Elsevier, Boston, Jun. 2, 2018. vil. 21, No. 2, pp. 232-239.

Yusuke Takahashi et al: "Accurate Estimation of the Duration of Testicular Ischemia Using Creatine Chemical Exchange Saturation Transfer (CrCEST) Imaging", Journal of Magnetic Resonance Imaging, Dec. 17, 2020, vol. 53, No. 5, pp. 1559-1567.

Office Action issued Dec. 2, 2025 in Japanese Patent Application No. 2022-566969, with English-language Translation.

P12    P1

P11-1    P11-2

P2

P21-1    P21-2 after 1 week Cryptorchidism after 6 weeks Cryptorchidism

A B

Upper half of Testis is
shielded by Lead Plate

Testis Testis

C D (%)

Head
Side

10

Tail
Side

0

E

Testicular CrCEST

MTR(%)

9
8
7
6
5
4
3
2
1
0

Shielded Non-shielded
Testis Testis

F

Johnsen score
(Pathological Score)

Johansen score

10

8

6

4

2

0

Shielded Non-shielded
Testis Testis

EVALUATION METHOD, PROGRAM, AND EVALUATION SYSTEM

TECHNICAL FIELD

The present disclosure generally relates to evaluation methods, programs (computer programs), and evaluation systems. In particular, the present disclosure relates to an evaluation method, a program (computer program) and an evaluation system in relation to a testicular function of an organism.

BACKGROUND ART

According to World Health Organization (WHO), infertility is defined by the failure to achieve a pregnancy after twelve months or more of regular unprotected sexual intercourse. The male is considered to cause infertility in an almost half of infertility cases including cases where only the male causes fertility and cases where both causes fertility.

In the male infertility, cases are classified into hypospermia when the ejected semen has a low volume, oligospermia when the semen contains less than the normal number of spermatozoa, and azoospermia when the semen contains no spermatozoa. Even in the azoospermia case, it is confirmed that part of the testis produces a very small amount of spermatozoa. Retrieval of spermatozoa is conducted by the microdissection testicular sperm extraction (Micro TESE) which tries to retrieve the spermatozoa from the testis with observation of the inside the testis using a microscope. However, this method includes noninvasive treatment of the testis accompanied with pain, and the extraction proportion is 30 to 40% and low.

Torsion of testis is one of diseases which causes serious dysfunction in the testicular function. The torsion of testis occurs when a testis rotates, twisting a spermatic cord that brings blood to the testis. It is known that necrosis of the testis may occur after six hours or more from stop of blood to the testis. It is necessary to perform orchiopexy which is a surgery to incise the scrotum and remedy the twist of the spermatic cord to stabilize blood transfer. Generally, appropriate time of performing the orchiopexy is from six to eight hours from symptoms appearing. A testis rescue percentage rapidly decreases with time and decreases to less than 10% after twenty-four hours from symptoms appearing. If the testis has already died, removal of the testis is required.

The degree of testicular damage is determined based on the duration of ischemia and the severity. However, if twisting is incomplete or intermittent, estimation of the degree of damage based on the duration of symptoms tends to give an estimated value excessively higher than its actual value. Especially, in many cases the duration of symptoms cannot be determined accurately in pediatric patients. Therefore, decision whether to perform orchiopexy depends on doctor's experience greatly.

Non Patent Literature 1 discloses that based on results of measurement using single voxel proton magnetic resonance spectroscopy (1H-MRS) in infertile men and control subjects, choline, creatine, myo-inositol, and the like are expected to biomarkers of the testicular function. However, it is unclear that it is useful for evaluation of duration of testicular ischemia and it is difficult to evaluation a location where the testicular function works.

CITATION LIST

Non Patent Literature

Non Patent Literature 1:P. Storey et al., Invest Radiol. 2018 February; 53(2): 87-95

SUMMARY OF INVENTION

Technical Problem

There is demand for noninvasive and accurate evaluation of a testicular function. There is further demand for a method for accurate evaluation of a location where a testicular function works.

The present disclosure aims to provide an evaluation method, a program and an evaluation system capable of presenting a result of noninvasive and accurate evaluation of a testicular function for each part of a testis.

Solution to Problem

An aspect of the present disclosure is an evaluation method performed by an arithmetic circuit, including obtaining processing, evaluation processing and presentation processing. The obtainment processing obtains image information on a sectional image representing an interested section of an organism including a target section of a testis of the organism generated by use of magnetic resonance of hydrogen atoms, and concentration information on a creatine concentration in the interested section measured by use of magnetic resonance based on chemical exchange saturation transfer. The evaluation processing generates an evaluation image representing a distribution of evaluation results of a testicular function in the target section based on the concentration information. The presentation processing presents the sectional image and the evaluation image.

An aspect of the present disclosure is a program for performing the above evaluation method by the arithmetic circuit.

An evaluation system of one aspect of the present disclosure includes an arithmetic circuit configured to perform obtaining processing, evaluation processing and presentation processing. The obtainment processing obtains image information on a sectional image representing an interested section of an organism including a target section of a testis of the organism generated by use of magnetic resonance of hydrogen atoms, and concentration information on a creatine concentration in the interested section measured by use of magnetic resonance based on chemical exchange saturation transfer. The evaluation processing generates an evaluation image representing a distribution of evaluation results of a testicular function in the target section based on the concentration information. The presentation processing presents the sectional image and the evaluation image.

Advantageous Effects of Invention

The present disclosure is capable of presenting a result of noninvasive and accurate evaluation of a testicular function for each part of a testis.

DESCRIPTION OF EMBODIMENTS

Hereinafter, embodiments will be described in detail with reference to appropriate drawings. Note that, description more detailed than necessary will be omitted. For example, detailed description of well-known matters or duplicate description of substantially the same components may be omitted. This aims to avoid the following description from becoming more redundant than necessary and to facilitate understanding of persons skilled in the art. The inventor(s) provides the following description and attached drawings for making persons skilled in the art understand the present disclosure only and has no intention to limit subject matters claimed in claims.

EMBODIMENTS

1. Outline

Figure 1:
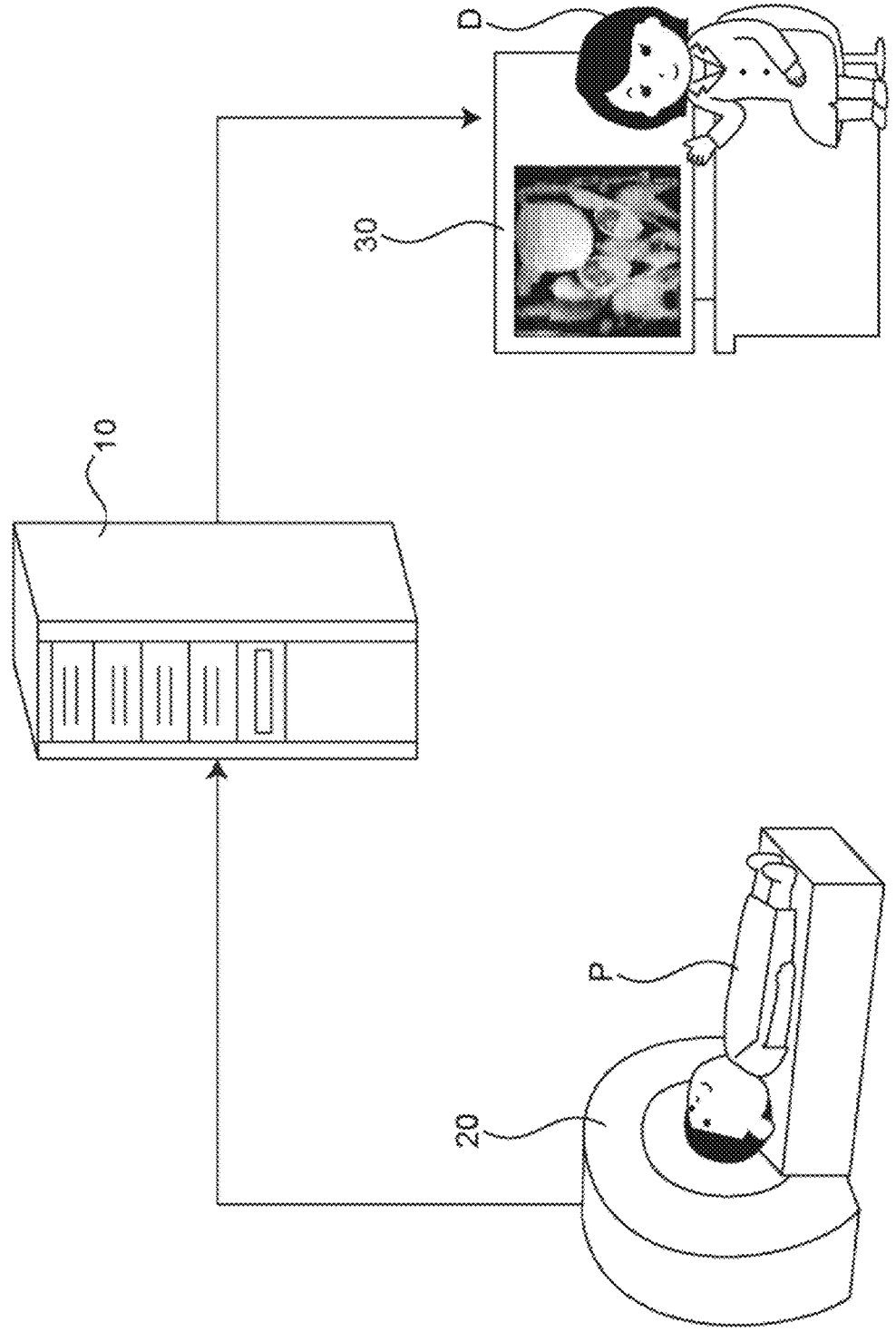
FIG. 1 is a diagram of an evaluation system of an embodiment.

FIG. 1 is an outline of an evaluation system 1 of an embodiment. The evaluation system 1 performs an evaluation method for evaluation of a function of target organ of an organism P. In the present embodiment, the target organ is a testis. In FIG. 1, the organism P is a patient (human being) and a result of evaluative by the evaluation system 1 can be used for a diagnosis of a patient by a doctor D, assistance of a diagnosis, or the like.

Figure 2:
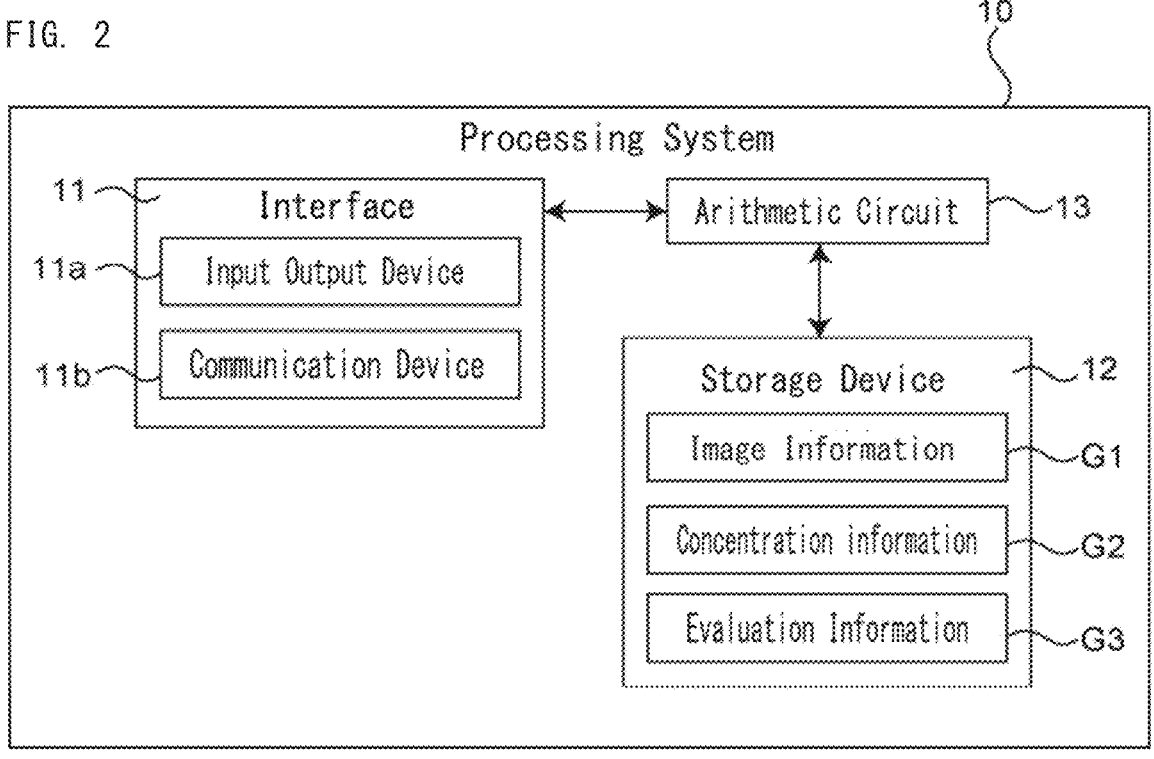
FIG. 2 is a block diagram of an evaluation system of FIG. 1.
Figure 3:
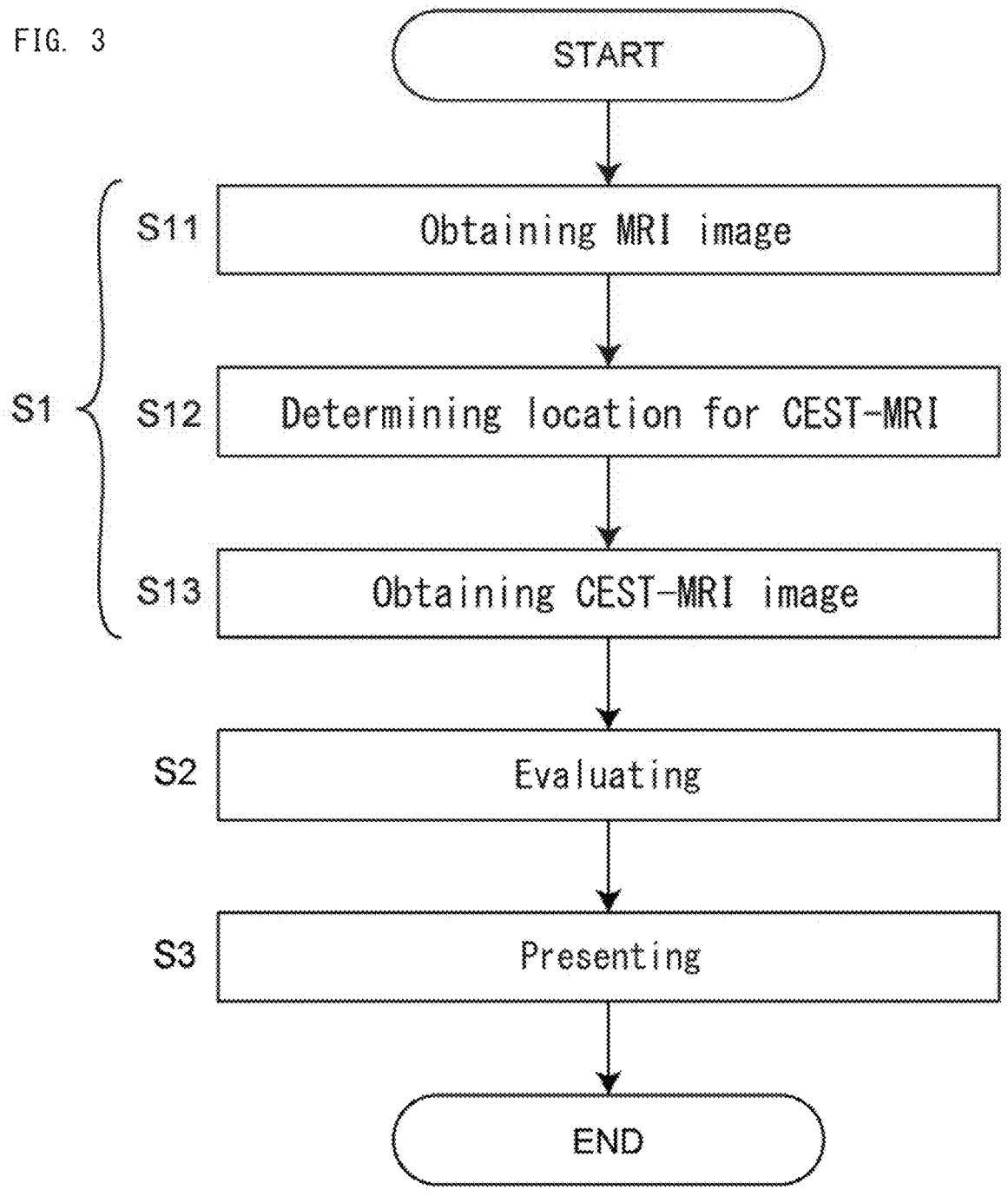
FIG. 3 is a flowchart of an evaluation method performed by the evaluation system of FIG. 1.

The evaluation system 1 includes a processing system 10 and as shown in FIG. 2, the processing system 10 includes an arithmetic circuit 13. In the evaluation system 1, the evaluation method is performed by the arithmetic circuit 13. The evaluation method includes, as shown in FIG. 3, obtainment processing S1, evaluation processing S2, and presentation processing S3.

Figure 4:
FIG. 4 is a view of an example of a sectional image represented by image information.
Figure 5:
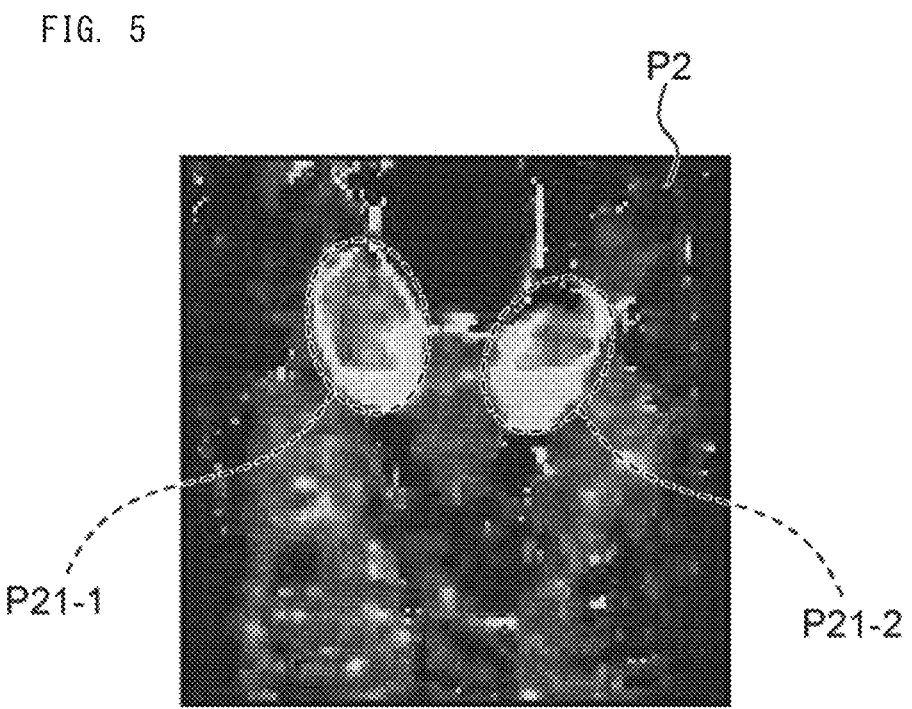
FIG. 5 is a view of an example of a concentration image represented by concentration information.

The obtainment processing S1 obtains image information G1 and concentration information G2. The image information G1 is information on a sectional image P1 (see FIG. 4) representing an interested section of the organism P generated by use of magnetic resonance of hydrogen atoms. The interested section includes a target section P11-1, P11-2 (hereinafter collectively designated by reference sign P11) of a testis of the organism P. The concentration information G2 is information on a target molecule concentration in the interested section, measured by use of magnetic resonance based on chemical exchange saturation transfer (CEST). The target molecule is a molecule in association with the function of the target organ. In the present embodiment, the target molecule is creatine. The concentration information G2 is, for example, as shown in FIG. 5, information on a concentration image P2 representing a distribution of creatine concentrations as a figure. The evaluation processing S2 generates an evaluation image P31-1, P31-2 (hereinafter collectively designated by reference sign P31) (see FIG. 7) representing a distribution of evaluation results of a testicular function in the target section P11 based on the concentration information G2. The presentation processing S3 presents the sectional image P1 and the evaluation image P31.

As described in more detail in "[3. EXAMPLES OF EVALUATION]", the testicular function of the organism P can be evaluated accurately by the creatine concentration of the testis. Additionally, the image information G1 and the concentration information G2 regarding the organism P both are obtained by use of magnetic resonance. The magnetic resonance is noninvasive. Therefore, the evaluation method enables noninvasive and accurate evaluation of the testicular function. In addition, according to the evaluation method, the evaluation image P31 representing a distribution of evaluation results of the testicular function in the target section P11 based on the concentration information G2 is generated and then presented together with the sectional image P1. Thus, a result of evaluation of the testicular function is presented for each part of the testis. Accordingly, the present embodiment enables presentation of the result of noninvasive and accurate evaluation of the testicular function for each part of the testis.

2. Details

Hereinafter, the evaluation system 1 of the present embodiment will be described in detail. As shown in FIG. 1, the evaluation system 1 includes the processing system 10, a measurement system 20, and a presentation system 30. The processing system 10 is communicably connected to the measurement system 20 and the presentation system 30. The processing system 10 is communicably connected to the measurement system 20 and the presentation system 30 via a communication network, for example.

The communication network may include the Internet. The communication network may be constituted by not only a network in conformity with a single communication protocol but also multiple networks in conformity with different communication protocols. The communication network may be, for example, a LAN (Local Area Network) in a hospital. The communication protocol may be selected from one or more of known various wired and wireless communication standards. Examples of the wired communication standards may include standards such as Ethernet (registered trademark). Examples of the wireless communication standards may include standards such as IEEE 802.11, 4G, or 5G. The communication network may include data communication devices such as repeater hubs, switching hubs, bridges, gateways, routers, and the like.

The measurement system 20 is used in, for example, a hospital or a clinic, to obtain information regarding the organism P. The measurement system 20 is used to obtain information used for evaluation of the testicular function by the processing system 10. The information used for evaluation of the testicular function by the processing system 10 includes the image information G1 and the concentration information G2. The image information G1 is information on the sectional image P1 (see FIG. 4) representing the interested section of the organism P generated by use of magnetic resonance of hydrogen atoms. The interested section includes the target sections P11-1, P11-2 of the testes of the organism P. The sectional image P1 includes a non-target image P12 being an image of a region other than the target sections P11-1, P11-2. Note that, FIG. 4 shows not the whole of the interested section but part of the interested section. The concentration information G2 is information on a creatine concentration in the interested section, measured by use of magnetic resonance based on chemical exchange saturation transfer (CEST). The concentration information G2 is, for example, as shown in FIG. 5, information on the concentration image P2 representing a distribution of creatine concentrations as a figure. The concentration image P2 indicates the distribution of creatine concentration by colors. Since the interested section includes the target sections P11-1, P11-2 of the testes of the organism P, the concentration image P2 includes target concentration images P21-1, P21-2 (hereinafter, collectively designated by reference sign P21) representing concentrations in the target sections P11-1, P11-2. Note that, FIG. 5 shows not the whole of the interested section but part of the interested section.

In the present embodiment, the measurement system 20 includes magnetic resonance imaging (MRI) apparatus. The measurement system 20 obtains, by the MRI apparatus, the image information G1 and the concentration information G2. Therefore, the sectional image P1 of the image information G1 is an MRI image of the organism P. Accordingly, the image information G1 includes the MRI image of the organism P as the sectional image P1. The concentration image P2 is a CEST-MRI image (Cr-CEST-MRI image) regarding creatine of the organism P. Accordingly, the concentration information G2 includes information on the CEST-MRI image regarding creatine of the organism P, as the information representing the creatine concentration in the interested section. In the present embodiment, the image information G1 and the concentration information G2 are obtained by use of the same MRI apparatus.

The presentation system 30 is used by the doctor D in a hospital, clinic, or the like, or an engineer or technologist in a testing company. The presentation system 30 is mainly used to output information from the processing system 10. The presentation system 30 includes one or more human machine interfaces. Examples of the human machine interfaces may include input devices such as keyboards, pointing devices (e.g., a mouse, a trackball mouse), or touch pads, output devices such as displays, loudspeakers, or input output devices such as touch panels. In the present embodiment, the presentation system 30 includes a display in order to display information from the processing system 10 by use of images. The information from the processing system 10 includes, for example, evaluation information G3. The evaluation information G3 is generated at the processing system 10 to present the sectional image P1 and the evaluation image P31. The presentation system 30 receives the evaluation information G3 from the processing system 10 and presents it. In the present embodiment, the presentation system 30 is realized by a single terminal device. The terminal device may be realized by a personal computer (a desktop computer, a laptop computer), mobile terminal (a smartphone, a tablet terminal, a wearable terminal, or the like), or the like.

The processing system 10 is used in the evaluation system 1 to perform the evaluation method. The processing system 10 includes, as shown in FIG. 2, an interface 11, a storage device 12, and the arithmetic circuit 13. The processing system 10 is realized by, for example, a server or a terminal device. The terminal device may be realized by a personal computer (a desktop computer, a laptop computer), mobile terminal (a smartphone, a tablet terminal, a wearable terminal, or the like), or the like.

The interface 11 includes an input output device 11*a* and a communication device 11*b*. The input output device 11*a* functions as an input device for inputting information to the processing system 10 and an output device for outputting information from the processing system 10. The input output device 11*a* includes one or more human machine interfaces. Examples of the human machine interfaces may include input devices such as keyboards, pointing devices (e.g., a mouse, a trackball mouse), or touch pads, output devices such as displays, loudspeakers, or input output devices such as touch panels. The communication device 11*b* is communicably connected to external devices or systems. The communication device 11*b* is used for communication with the measurement system 20 and the presentation system 30 via communication network(s). The communication device 11*b* includes one or more communication interfaces. The communication device 11*b* is connectable to communication network(s) and has functionality to perform communication via the communication network(s). The communication device 11*b* complies with a predetermined communication protocol. The predetermined communication protocol may be selected from one or more of known various wired and wireless communication standards.

The storage device 12 is used for storing information used by the arithmetic circuit 13 and information generated by the arithmetic circuit 13. The storage device 12 includes one or more storages (non-transitory storage media). The storages may be selected from one or more of hard disk drives, optical drives, or solid state drives (SSD). Further, the storages may be any one of an internal type, an external type or a NAS (network-attached storage) type.

Information to be stored in the storage device 12 includes the image information G1, the concentration information G2, and the evaluation information G3. FIG. 2 shows that the storage device 12 stores all of the image information G1, the concentration information G2, and the evaluation information G3. The image information G1, the concentration information G2, and the evaluation information G3 always need not be stored in the storage device 12 but may be stored in the storage device 12 when the arithmetic circuit 13 requires them. In particular, the evaluation information G3 is stored in the storage device 12 after generated by the arithmetic circuit 13.

The arithmetic circuit 13 is circuitry for controlling operations of the processing system 10. The arithmetic circuit 13 is connected to the interface 11 and is accessible to the storage device 12. The arithmetic circuit 13 can be realized by a computer system including one or more processors (microprocessors) and one or more memories, for example. The one or more processors realizes functions as the arithmetic circuit 13 by executing program(s) (stored in the one or more memories or the storage device 12). The program(s) herein may be stored in the storage device 12 in advance but can be provided through telecommunication circuit such as the Internet or as in form of stored in a non-transitory storage medium such as a memory card.

The arithmetic circuit 13, as shown in FIG. 3, is configured to perform the obtainment processing S1, the evaluation processing S2, and the presentation processing S3.

The obtainment processing S1 obtains the image information G1 and the concentration information G2. As described above, the image information G1 and the concentration information G2 are obtained by the MRI apparatus of the measurement system 20. As mentioned before, the image information G1 includes the MRI image of the organism P as the sectional image P1 representing the interested section. As explained above, the concentration information G2 includes the information on the concentration image P2 as the information representing the creatine concentrations in the interested section, and the concentration image P2 is the CEST-MRI image regarding creatine of the organism P.

Figure 6:
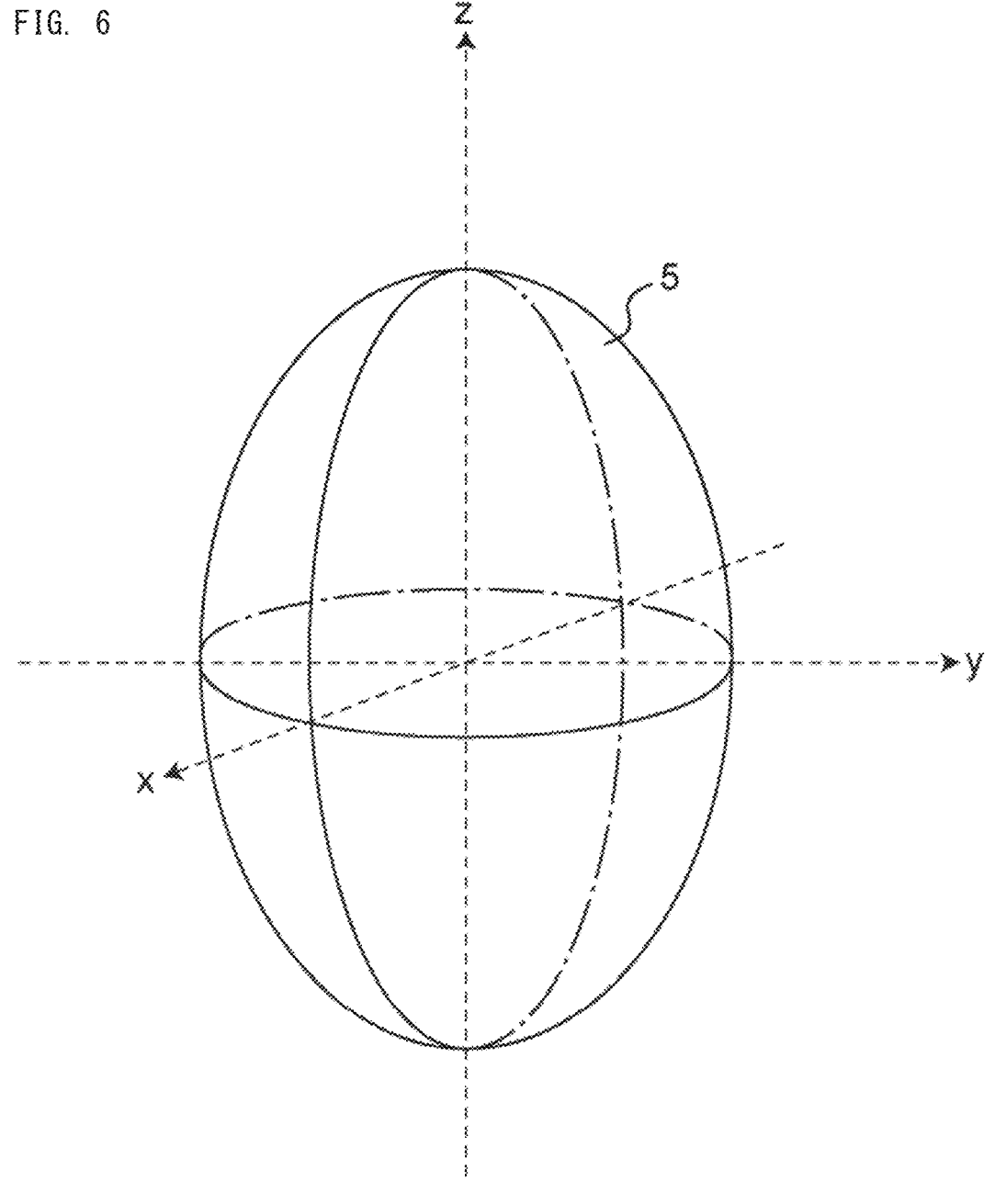
FIG. 6 is a schematic diagram of a testis.

A testis is a three-dimensional object, and a three-dimensional shape of the testis is not a sphere but can be represented approximately by an ellipsoid 5 as shown in FIG. 6. Therefore, a size of the target section P11 depends on how to take an MRI image (the sectional image P1). An increase in the size of the target section P11 leads to an increase in an amount of information on creatine concentrations in the target section P11. In the present embodiment, to obtain the target section P11 with a larger size, the obtainment processing S1 includes, as shown in FIG. 3, first processing S11, second processing S12, and third processing S13.

The first processing S11 obtains a plurality of MRI images an interested section of each of which is perpendicular to a predetermined direction, from the organism P. For example, the first processing S11 obtains MRI images at a regular interval along the predetermined direction. In this case, interested sections represented by the plurality of MRI images are arranged at the regular interval along the predetermined direction. This facilitates understanding of the three-dimensional shape of the testis. The first processing S11 uses the MRI apparatus of the measurement system 20. In the first processing S11, the predetermined direction is determined to allow the plurality of MRI images includes an MRI image with a largest sectional area of the testis. As shown in FIG. 6, the testis is represented by the ellipsoid 5. In the case of the ellipsoid 5 of FIG. 6, the testis has a maximum sectional area when the ellipsoid 5 has a maximum sectional area. In the ellipsoid 5 of FIG. 6, a diameter in a z-axis direction is the longest, a diameter in a y-axis direction is the second longest, and a diameter in an x-axis direction is the shortest. Therefore, the sectional area of the ellipsoid 5 of FIG. 6 becomes the largest at a yz plane. When the x-axis direction can be selected as the predetermined direction, it is possible to obtain an MRI image with the largest sectional area of the testis. Since the organism P has two testes, a sectional area of either one of the two testes or a total sectional area of the two testes can be considered as a sectional area of a testis. Note that, determination of the target section P11 in the sectional image P1 can be done by manually or automatically by means of image processing.

The second processing S12 determines a main MRI image which is the largest in an area of the target section P11 among the plurality of MRI images. In more detail, the second processing S12 selects an MRI image which is the largest in the area of the target section P11 among the plurality of MRI images obtained in the first processing S11, as the main MRI image. Information on the main MRI image is used in the image information G1.

The third processing S13 obtains a CEST-MRI image about an interested section of the main MRI image. In more detail, the third processing S13 measures a creatine concentration in the interested section of the main MRI image. The third processing S13 utilizes the MRI apparatus of the measurement system 20 to measure the creatine concentration. The first processing S11 and the third processing S13 utilize the same MRI apparatus. This allows obtainment of the MRI image and the CEST-MRI image by the same imaging system and facilitates determining a locational relationship between the MRI image and the CEST-MRI image. The third processing S13 can provide information on the CEST-MRI image corresponding to the main MRI image.

In addition, the third processing S13 obtains a CEST-MRI image about an interested section represented by at least one of auxiliary MRI images prior and subsequent to the main MRI image among the plurality of MRI image obtained by the first processing S11 in the predetermined direction. In the present embodiment, the third processing S13 obtains the CEST-MRI images about the interested sections represented by both the auxiliary MRI images prior and subsequent to the main MRI image among the plurality of MRI image obtained by the first processing S11 in the predetermined direction. The testis is a three-dimensional object, and creatine concentrations in the testis is distributed in three-dimensionally. Therefore, by obtaining, in addition to the main MRI image, a CEST-MRI image about an interested section represented by at least one of auxiliary MRI images prior and subsequent to the main MRI image among the plurality of MRI image in the predetermined direction, it is possible to conduct three-dimensional evaluation of creatine concentrations in the testis. Therefore, according to the third processing S13, information on the CEST-MRI image(s) corresponding to the auxiliary MRI image(s) can be obtained in addition to the CEST-MRI image corresponding to the main MRI image.

The image information G1 obtained by the obtainment processing S1 described above includes information on the main MRI image. The concentration information G2 obtained by the obtainment processing S1 includes information on the CEST-MRI image corresponding to the main MRI image. Further, the concentration information G2 includes information on the CEST-MRI image(s) corresponding to the auxiliary MRI image(s).

The evaluation processing S2 generates the evaluation image P31 (see FIG. 7 and FIG. 8) based on the concentration information G2. The evaluation image P31 is an image representing a distribution of evaluation results of the testicular function in the target section P11. As mentioned before, the concentration information G2 includes information on the CEST-MRI image corresponding to the main MRI image and information on the CEST-MRI image(s) corresponding to the auxiliary MRI image(s). The evaluation processing S2 generates the evaluation image P31 based on information on the CEST-MRI image which is the highest in a representative value of the creatine concentration among information on CEST-MRI images included in the concentration information G2 (i.e., information on the CEST-MRI images respectively corresponding to the main MRI image and the auxiliary MRI image(s)). The representative value of the creatine concentration may be a statistical value such as an average value, a maximum value, or a mode value, about the creatine concentration. Use of the representative value make comparison between CEST-MRI images based on their creatine concentrations easier. As described above, the concentration image P2 includes the target concentration images P21-1, P21-2 representing concentrations in the target sections P11-1, P11-2. Locations of the target concentration images P21-1, P21-2 can be determined based on the target sections P11-1, P11-2 in the sectional image P1. Note that, FIG. 4 and FIG. 5 correspond to the same interested section but show the interested section partially, and therefore the locations of the target concentration images P21-1, P21-2 are not identical to locations of the target sections P11-1, P11-2.

Figure 7:
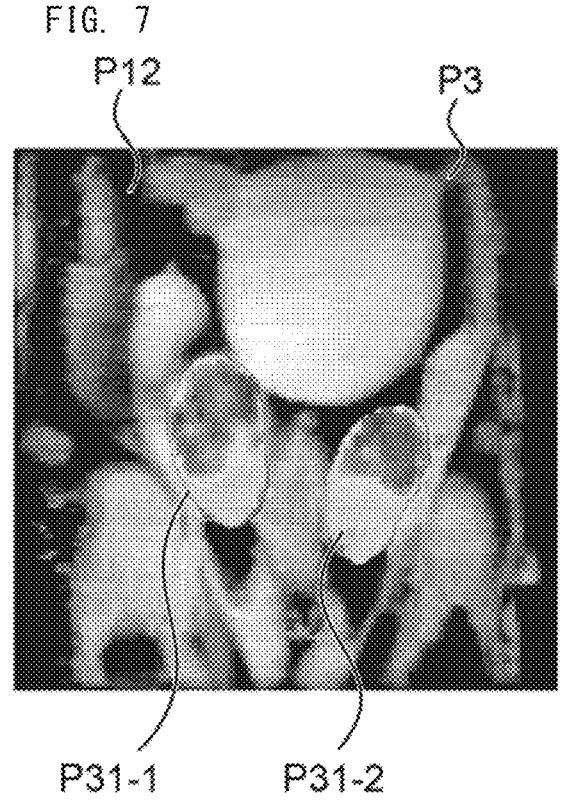
FIG. 7 is a view of one example of a synthesized image represented by an evaluation information.
Figure 8:
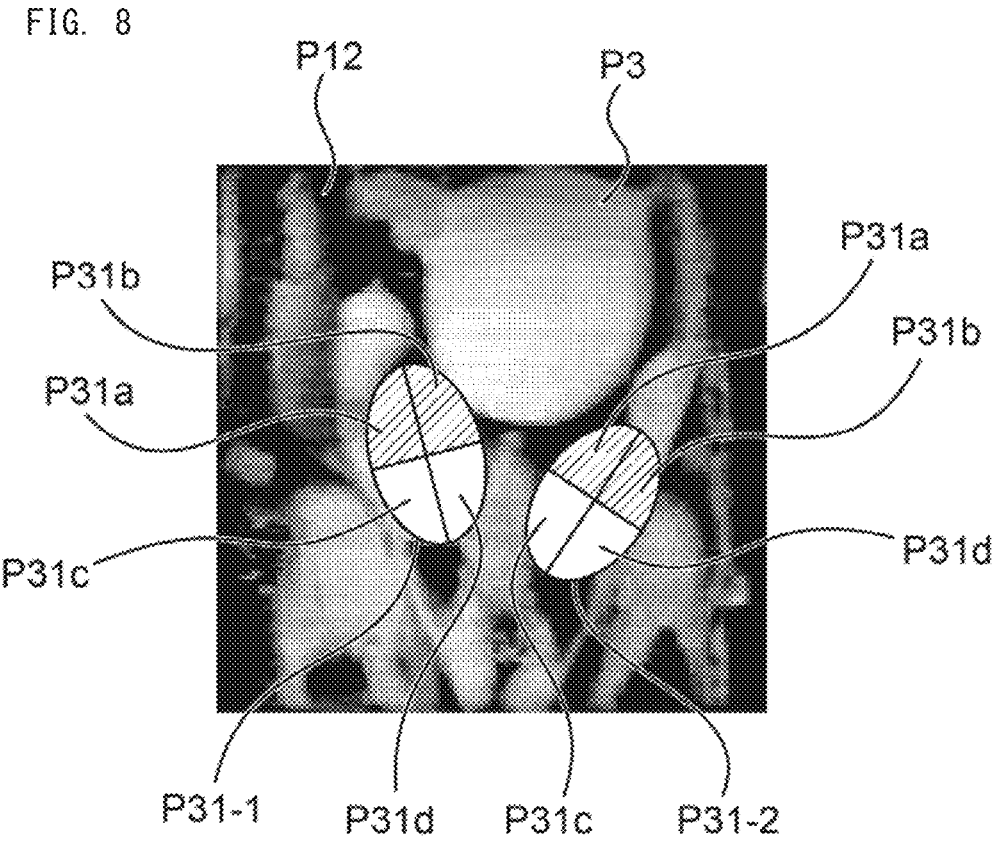
FIG. 8 is a view of another example of a synthesized image represented by an evaluation information.

The presentation processing S3 presents the sectional image P1 and the evaluation image P31. To present the sectional image P1 and the evaluation image P31, the presentation processing S3 generates the evaluation information G3. In the present embodiment, the presentation processing S3 presents the sectional image P1 and the evaluation image P31 by presenting a synthesized image P3. Thus, the evaluation information G3 includes information on the synthesized image P3. FIG. 7 and FIG. 8 show examples of the synthesized image P3. The synthesized image P3 is an image resulting from replacement of an image corresponding to the target section P11 in the sectional image P1 with the evaluation image P31. The "replacement" means either removing a part of an image corresponding to the target section P11 from the sectional image P1 and fitting the evaluation image P31 with substantially the same area to the removed part, or superimposing the evaluation image P31 on a part of an image corresponding to the target section P11 without removal of that part. In the present embodiment, as shown in FIG. 7 and FIG. 8, the synthesized image P3 may be constituted by a combination of the non-target image P12 in the sectional image P1 and the evaluation image P31, for example.

In FIG. 7, the evaluation image P31 is an image representing a distribution of creatine concentrations in the target section P11. As described in more detail in "[3. EXAMPLES OF EVALUATION]", it is confirmed that higher the creatine concentration higher the testicular function of the organism P. Therefore, the creatine concentration of the testis can be used as an indicator of the testicular function without any modifications.

In FIG. 8, the evaluation image P31 represents an evaluation result of the testicular function in each of a plurality of (four, in the illustrated example) portions P31a to P31d obtained by dividing the target section P11. The evaluation result of the testicular function may be not the creatine concentration as such but determined based on the creatine concentration. For example, the evaluation of the testicular function may be determined whether or not the creatine concentration of the testis exceeds a threshold value. When the creatine concentration exceeds the threshold value, the testicular function may be evaluated as in a normal state. When the creatine concentration is equal to or lower than the threshold value, the testicular function may be evaluated as in an abnormal state. The threshold value is a value for determining whether the testicular function is in the normal state or the abnormal state. The threshold value may be determined in consideration of the creatine concentration of the organism P with the testicular function being in the normal state, the creatine concentration of the organism P with the testicular function being in the abnormal state, and/or the like. In FIG. 8, the evaluation results indicates whether the testicular function is in the normal state or the abnormal state. In FIG. 8, the evaluation image P31 indicates results of evaluation of the testicular function based on whether or not the representative value of the creatine concentration of each of the portions P31a to P31d exceeds the threshold value. For example, the testicular function is evaluated as the normal state if the representative value of the creatine concentration exceeds the threshold value, and the testicular function is evaluated as the abnormal state if the representative value of the creatine concentration is equal to or smaller than the threshold value. For each of the portions P31a to P31d, the representative value of the creatine concentration may be a statistical value of the creatine concentration, such as, an average value, a maximum value, or a mode value. In relation to the evaluation image P31-1 of FIG. 8, for each of the portions P31a, P31b the testicular function is evaluated as the normal state, and for each of the portions P31c, P31d the testicular function is evaluated as the abnormal state. In relation to the evaluation image P31-2 of FIG. 8, for each of the portions P31a, P31b the testicular function is evaluated as the normal state, and for each of the portions P31c, P31d the testicular function is evaluated as the abnormal state.

The evaluation system 1 can present the synthesized image P3 by means of the input output device 11a of the interface 11, based on the evaluation information G3 obtained by the aforementioned manner. In addition, the evaluation system 1 can provide the evaluation information G3 to the presentation system 30 via the communication device 11b of the interface 11. The presentation system 30 can present the synthesized image P3 as shown in FIG. 7 or FIG. 8 based on the evaluation information G3 from the evaluation system 1.

3. Examples of Evaluation

In order to confirm that the testicular function can be evaluated by the creatine concentration, as described in examples 1 to 4 below, various testicular models were evaluated by use of Cr-CEST-MRI. From these examples 1 to 4, it is confirmed that higher the creatine concentration higher the testicular function of the organism P.

3-1. Example 1

Example 1 is evaluation of a mouse cryptorchidism model by Cr-CEST-MRI. Based on disclosure of S. Song et al., Urology, 82(3), September 2013, Pages 743.e17-743.e23, cryptorchidism model mice were produced. This mouse cryptorchidism model is a model where the right testis of the mouse is fixed in its abdominal cavity. Since the right testis is inside the abdominal cavity with a relatively high temperature, it is known that the testicular function decreases with time. The cryptorchidism model mice were subjected to Cr-CEST-MRI. FIG. 9 shows this result.

Figure 9A:
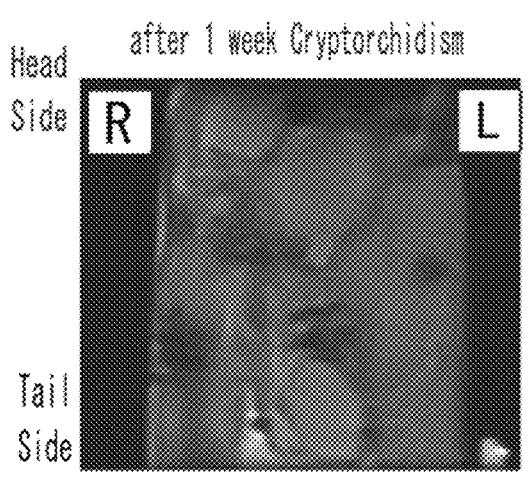
FIG. 9A is an explanatory view of evaluation of a mouse cryptorchidism model by CR-CEST-MRI.
Figure 9A:
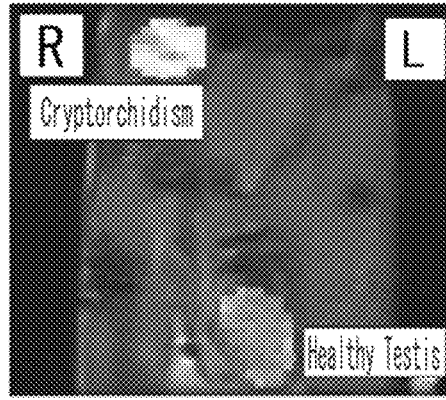
Figure 9A:
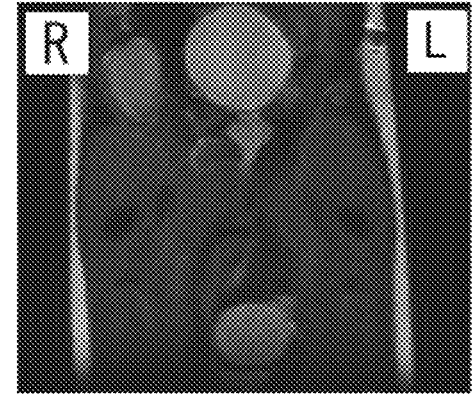
Figure 9A:
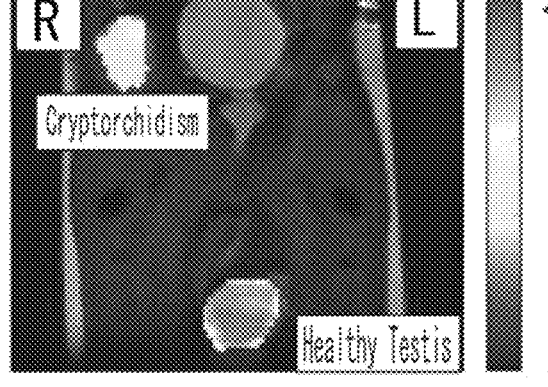
Figure 9B:
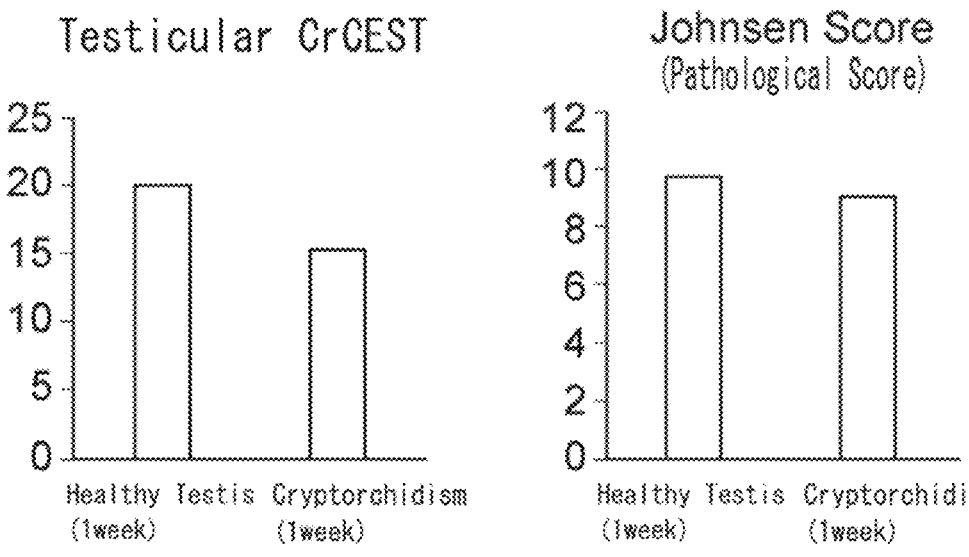
FIG. 9B is an explanatory view of evaluation of a mouse cryptorchidism model by CR-CEST-MRI.
Figure 9B:
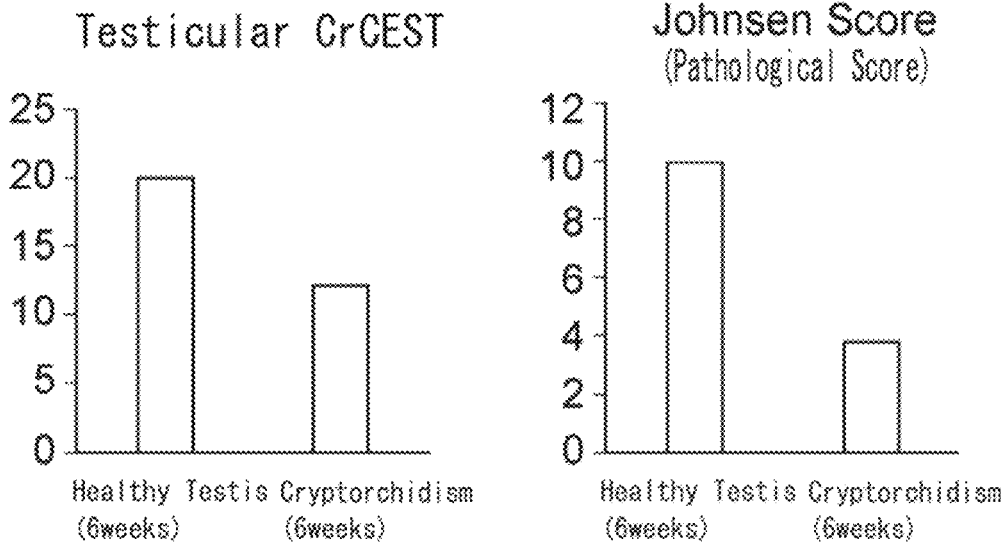

FIGS. 9A and 9B are explanatory views of evaluation of the mouse cryptorchidism model by CR-CEST-MRI. In FIG. 9A, upper images are T2 weighted images and lower images are Cr-CEST-MRI images. FIG. 9B shows graphs of comparison between intensity of testicular CrCEST and the Johnsen Score being a pathological score for infertility, for models after one week and six weeks from their cryptorchidism production.

As shown in FIG. 9A, the image indicates that the right testis with the decreased testicular function has a decreased CrCEST signal. As shown in FIG. 9B, the decrease in the CrCEST signal was found at the time after one week from the cryptorchidism production, and earlier than the decrease in the Johnsen score which is a noninvasive pathological diagnosis score for infertility testes actually used in clinical practice. This fact reveals that the CrCEST can evaluate the spermatogenesis function for the cryptorchidism models.

3-2. Example 2

EXAMPLE 2 is evaluation of a mouse testicular ischemia model by Cr-CEST-MRI. Based on disclosure of J S. Palmer et al., J Urol 1997; 158 (3 Pt 2): 1138-1140, testicular ischemia model mice were produced as a model for simulating testicular torsion. The testicular ischemia model mice were subjected to Cr-CEST-MRI.

All the image processing and data analysis were performed by use of scripts described in MATLAB (registered trademark) R2017b (The MathWorks, Inc., Natick, MA). The CrCEST effect was evaluated by magnetization transfer ratios (MTR) three point analysis determined by the following formula.

$$MTR_{Cr^{**}} = ([S_{1.5\,ppm} + S_{2.3\,ppm}]/2 - S_{1.9\,ppm})/S_0 \quad \text{(FORMULA 1)}$$

All the data are shown as averages plus-minus standard deviations. Statistical analysis was implemented by JMP14 (SAS Institute, Cary, NC). To compare two groups, a two-sided test of a paired t-test was conducted. For correlation analysis, Pearson's correlation coefficient (r) was calculated. The case of $P<0.05$ was considered as being statistically significant.

Figure 10:
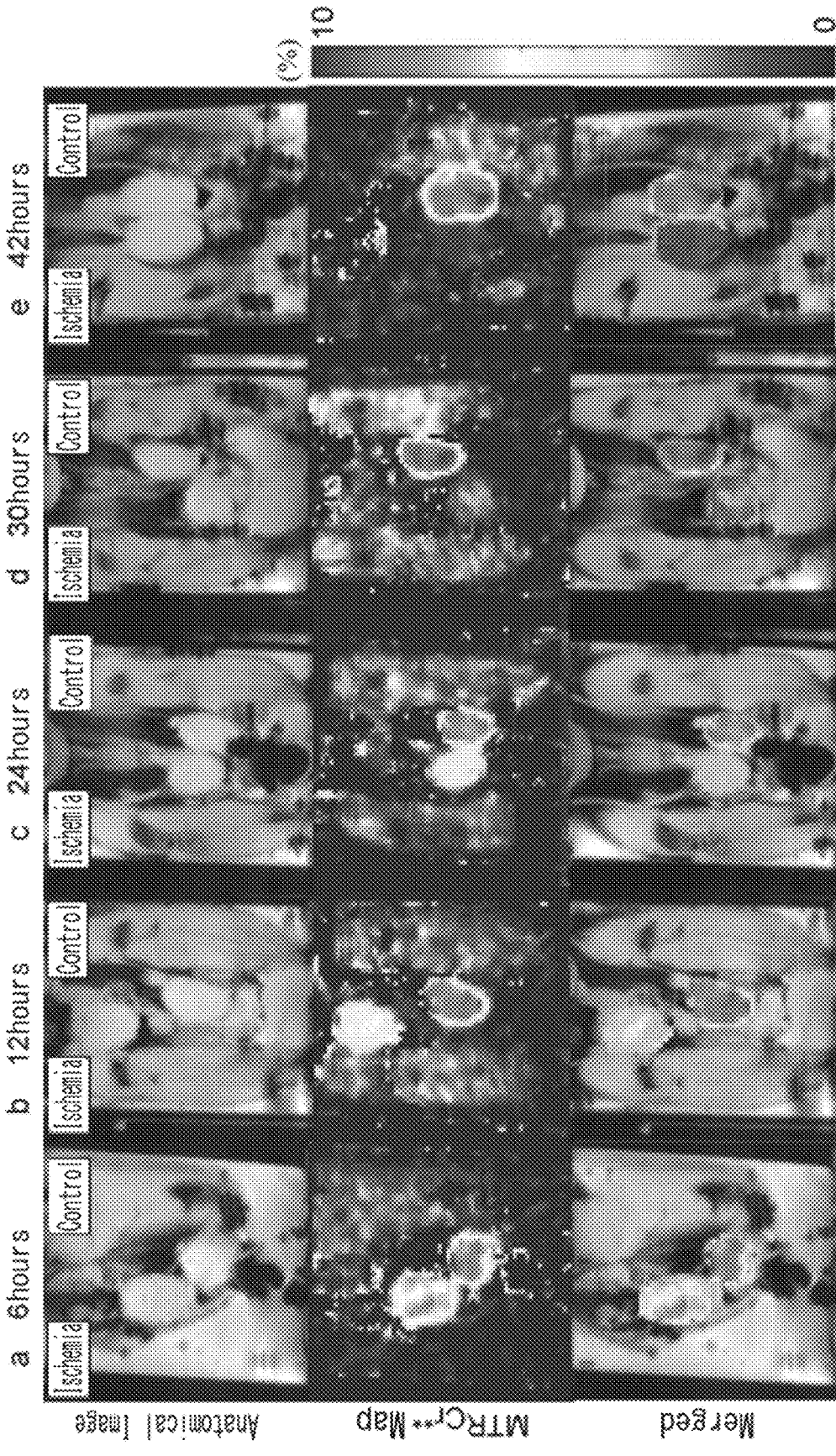
FIG. 10 is a view of CrCEST images about mouse testicular ischemia models.

FIG. 10 shows the result. FIG. 10 is a view of the CrCEST images about the mouse testicular ischemia models. The anatomical images do not give opinions of obvious abnormal state. However, the ischemia testis shows a decrease in $MTR_{Cr^{}}$ in comparison with the control testis even if the ischemia duration is shorter than six hours. $MTR_{Cr^{}}$ was continuously decreased after twenty four hours. This was considered to cause the irreversible testicular dysfunction.

Figure 11:
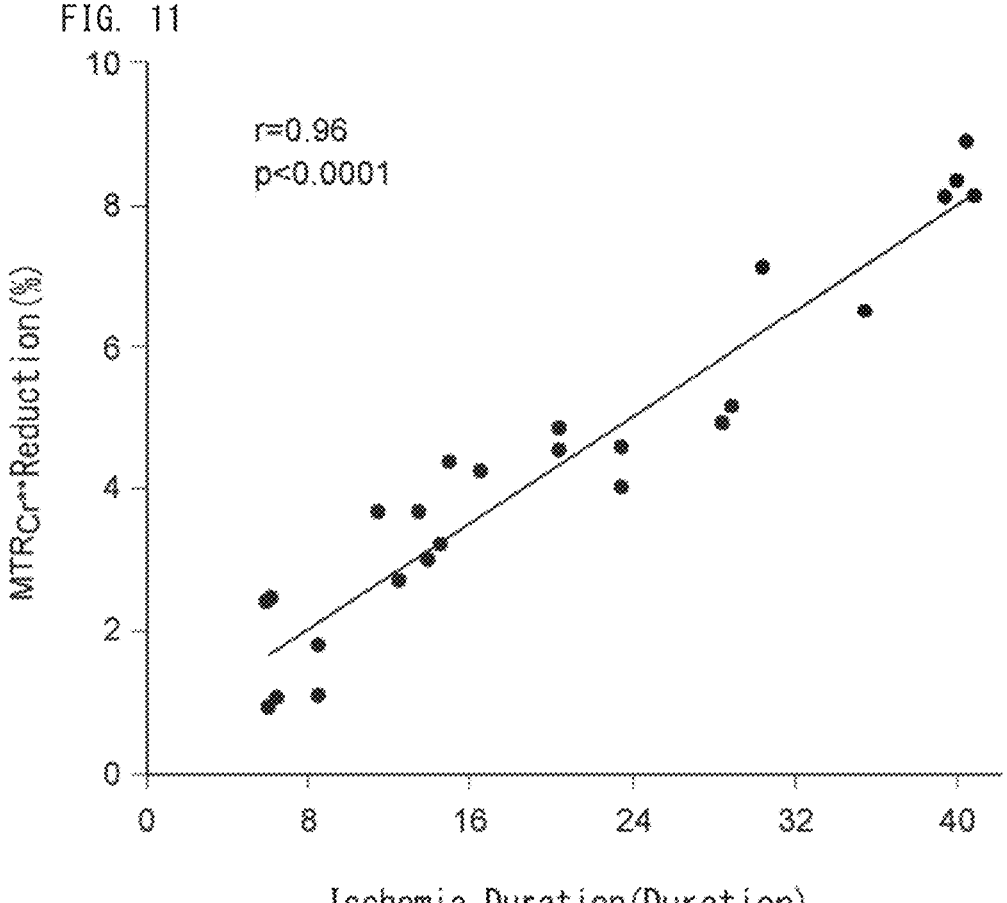
FIG. 11 is a graph showing a correlation between a CrCEST effect and a duration of ischemia about a mouse testicular ischemia model.

Further, to reveal a relation between the CrCEST effect and a duration of ischemia, correlation analysis was conducted. FIG. 11 shows the result. FIG. 11 is a graph showing the correlation between the CrCEST effect and the duration of ischemia about the mouse testicular ischemia model. There has been seen a strong linear correlation between a decrease in $MTR_{Cr^{}}$ and the duration of the testicular ischemia ($r=0.96$, $p<0.0001$). This result indicates that evaluation of the decrease in $MT_{RCr^{}}$ can give accurate estimation of the duration of the testicular ischemia.

3-3. Example 3

EXAMPLE 3 is evaluation of a testicular model locally exposure to ionizing radiation, by Cr-CEST-MRI. In male infertility, it is known that the spermatogenesis function inside the testis is not decreased uniformly but is different at a different part. Whether or not the spermatogenesis function could be examined for each part inside the testis was tested by the testicular model locally exposure to ionizing radiation. Only a lower half of the testis was exposed to ionizing radiation (6Gy) with an upper half of the testis being blocked or shielded by a lead plate. The testicular model mice locally exposure to ionizing radiation were subjected to Cr-CEST-MRI.

Figure 12:
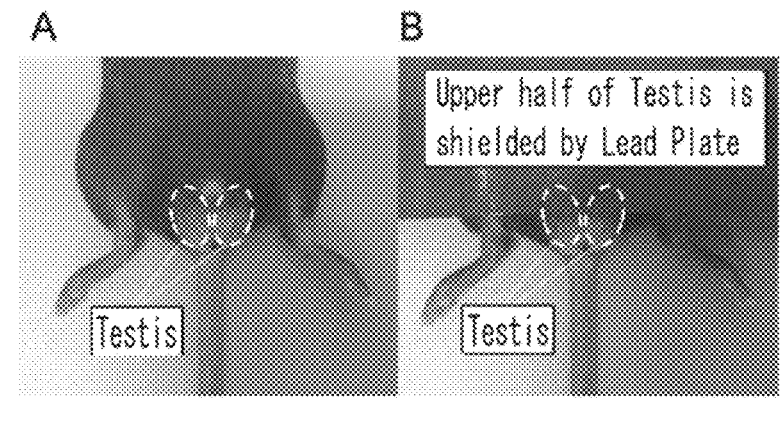
FIG. 12 is an explanatory view of evaluation of a testicular model locally exposure to ionizing radiation, by Cr-CEST-MRI.
Figure 12:
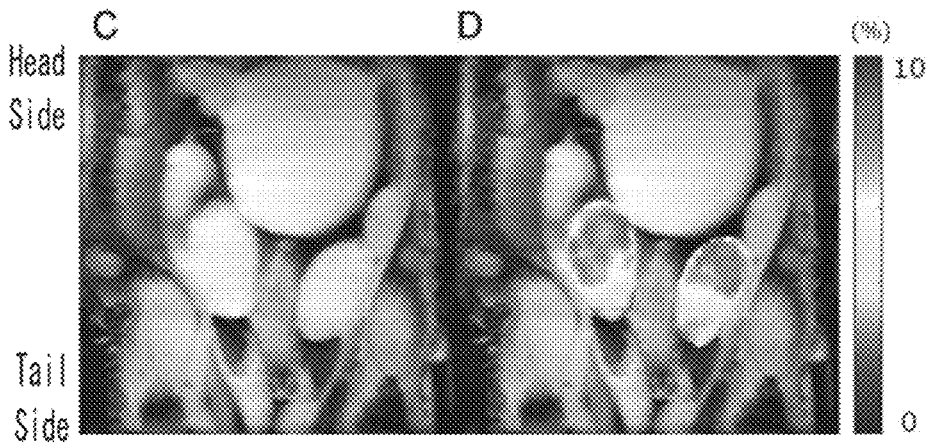
Figure 12:
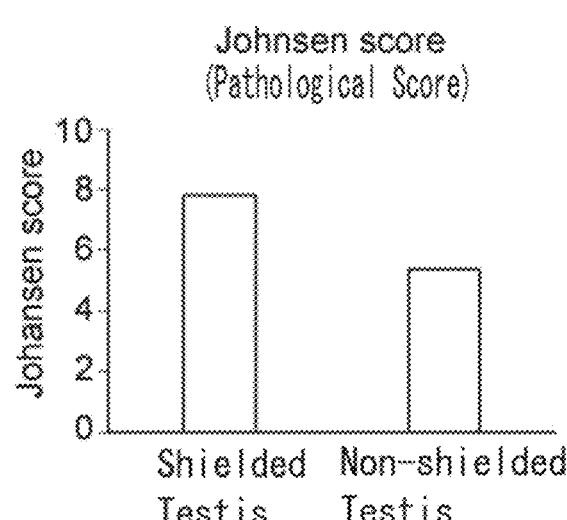

FIG. 12 shows the result. FIG. 12 is an explanatory view of evaluation of the testicular model locally exposure to ionizing radiation, by Cr-CEST-MRI. As shown in A of FIG. 12 and B of FIG. 12, the upper half of each testis was shielded and the mouse was exposed to ionizing radiation (6Gy). C of FIG. 12 and D of FIG. 12 are Cr-CEST-MRI images. A decrease in a CrCEST signal of the lower half of the testis exposed to ionizing radiation is found. E of FIG. 12 and F of FIG. 12 are graphs of comparison between CrCEST signal and Johnsen score for a non-shielded testis and a shielded testis. As shown in D of FIG. 12, E of FIG. 12, and F of FIG. 12, a decrease in the Cr-CEST signal and a decrease in the Johnsen score are found in the lower half of the testis exposed to ionizing radiation. This reveals that the testicular Cr-CEST MRI enables examination of the spermatogenesis function for each part inside the testis.

3-4. Example 4

EXAMPLE 4 is evaluation of a drug-induced testicular function model using a mouse by Cr-CEST-MRI. As the drug-induced testicular function model, an anticancer drug dosed model was used. It is known that dose of anticancer drug cause the male fertility. Therefore, the anticancer drug dosed model was used for evaluation of the male fertility. The anticancer drug used was cisplatin used for treatment of the testicular cancer. The anticancer drug dosed model was prepared by subjecting a mouse to a single dose of cisplatin into the abdominal cavity (15 mg/kg).

Figure 13:
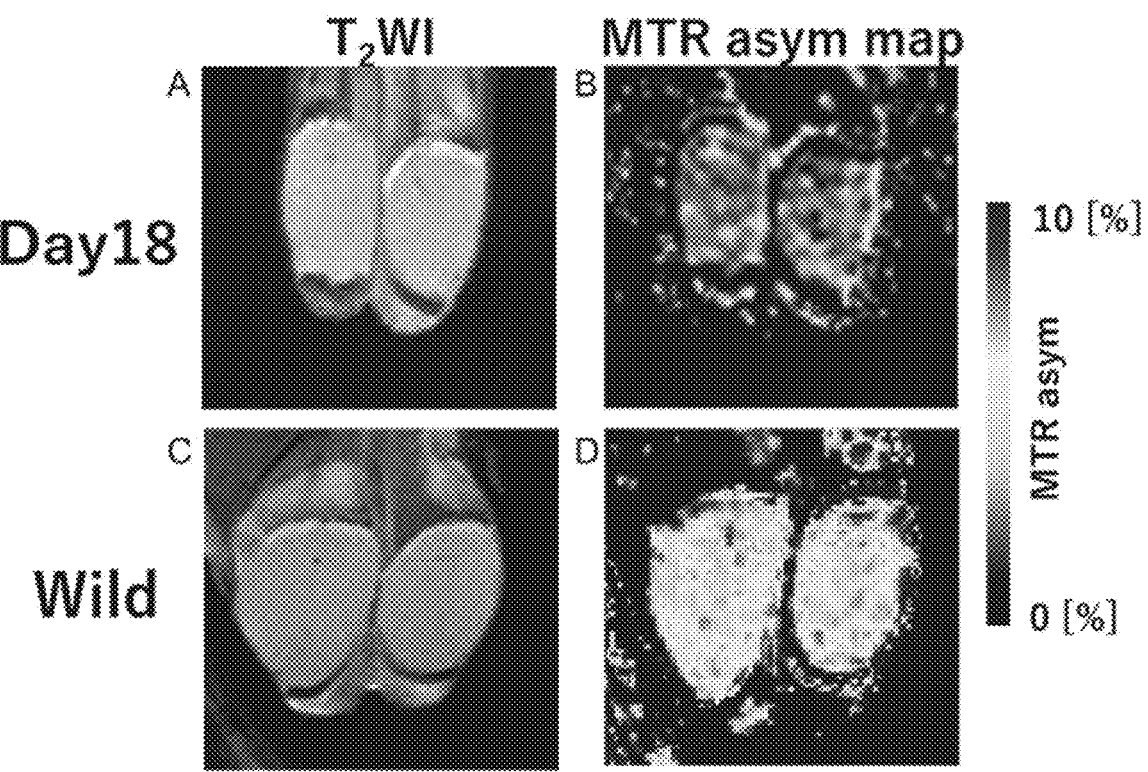
FIG. 13 is an explanatory view of evaluation of a drug-induced testicular function model with a dose of a mouse anticancer drug (cisplatin), by Cr-CEST-MRI.

FIG. 13 shows a result of evaluation of the anticancer drug dosed model using a mouse. FIG. 13 is an explanatory view of evaluation of the anticancer drug dosed model mouse, by Cr-CEST-MRI. A of FIG. 13 is a T2 weighted image of the anticancer drug dosed model of Day 18 after dose, and B of FIG. 13 is a Cr-CEST-MRI image of the anticancer drug dosed model mouse of Day 18 after dose. C of FIG. 13 is T2 weighted image of a control (a mouse not dosed with cisplatin), and D of FIG. 13 is a Cr-CEST-MRI image of the control.

According to the T2 weighted images shown in A of FIG. 13 and C of FIG. 13, a clear difference could not be found between the anticancer dosed model and the control. According to the Cr-CEST-MRI images shown in B of FIG. 13 and D of FIG. 13, the Cr-CEST signal was found to be lower in the testis of the anticancer dosed model than in the testicular of the control. The anticancer dosed models reveals that the testicular Cr-CEST MRI enables evaluation of the spermatogenesis function.

4. Examples of Applications

The evaluation system 1 described above can be available in various scenes. The evaluation system 1 can be considered to be used in the scene of the microdissection testicular sperm extraction, for example. The scene of the microdissection testicular sperm extraction is considered to include a scene of consideration of performing the microdissection testicular sperm extraction, and a scene of retrieval of spermatozoa by performing the microdissection testicular sperm extraction.

In the scene of consideration of performing the microdissection testicular sperm extraction, the doctor D can diagnose the testicular function for each part of a testis of the organism P from the synthesized image P3 obtained from the evaluation information G3, based on the knowledge that higher the creatine concentration higher the testicular function of the organism P. Concretely, the doctor D can determine, from the synthesized image P3, whether or not it is possible to retrieve spermatozoa by the microdissection testicular sperm extraction. For example, according to the synthesized image P3 of FIG. 8, in relation to the evaluation image P31-1, for each of the portions P31a, P31b the testicular function is evaluated as the normal state, and for each of the portions P31c, P31d the testicular function is evaluated as the abnormal state. Accordingly, it can be considered that there is a high possibility of retrieving spermatozoa from parts of the testis corresponding to the portions P31a, P31b of the evaluation image P31-1 and there is a low possibility of retrieving spermatozoa from parts of the testis corresponding to the portions of P31c, P31d of the evaluation image P31-1. If the testis contains part the testicular function of which is the normal state, the possibility of retrieving spermatozoa by performing the microdissection testicular sperm extraction is determined to be high.

In the scene of retrieval of spermatozoa by performing the microdissection testicular sperm extraction, the doctor D can determine which part of a testis of the organism P, as a search target for spermatozoa, from the synthesized image P3 obtained from the evaluation information G3, based on the knowledge that higher the creatine concentration higher the testicular function of the organism P. The microdissection testicular sperm extraction is highly invasive, and puts heavy burden on a patient. Therefore, it is considered to select not a whole of the testis but only part of the testis where the possibility of retrieving spermatozoa is high, as the search target for spermatozoa. For example, according to the synthesized image P3 of FIG. 8, in relation to the evaluation image P31-1, for each of the portions P31a, P31b the testicular function is evaluated as the normal state, and for each of the portions P31c, P31d the testicular function is evaluated as the abnormal state. Accordingly, it can be considered that there is a high possibility of retrieving spermatozoa from parts of the testis corresponding to the portions P31a, P31b of the evaluation image P31-1 and there is a low possibility of retrieving spermatozoa from parts of the testis corresponding to the portions of P31c, P31d of the evaluation image P31-1. Therefore, in the microdissection testicular sperm extraction, searching parts of the testis corresponding to the portions P31a, P31b for spermatozoa can keep high possibility of retrieving spermatozoa but reducing the burden on the patient, relative to searching the entire testis.

5. Advantageous Effects

In the embodiment described above, the evaluation method is performed by the arithmetic circuit 13 and includes the obtainment processing S1, the evaluation processing S2, and the presentation processing S3. The obtainment processing S1 obtains obtaining the image information G1 on the sectional image P1 representing the interested section of the organism P including the target section P11 of the testis of the organism P generated by use of magnetic resonance of hydrogen atoms, and the concentration information G2 on the creatine concentration in the interested section measured by use of magnetic resonance based on chemical exchange saturation transfer. The evaluation processing S2 generates the evaluation image P31 representing the distribution of the evaluation results of the testicular function in the target section P11 based on the concentration information G2. The presentation processing S3 presents the sectional image P1 and the evaluation image P31. Accordingly, this configuration is capable of presenting a result of noninvasive and accurate evaluation of a testicular function for each part of a testis.

Further in the present embodiment, the presentation processing S3 presents the sectional image P1 and the evaluation image P31 by presenting the synthesized image P3 resulting from replacement of an image corresponding to the target section P11 in the sectional image P1 with the evaluation image P31. Accordingly this configuration can present a relation between a location of the testis in the sectional image P1 and a distribution of evaluation results of the testicular function represented by the evaluation image P31 in an easy-to-understand way.

Further in the present embodiment, the evaluation image P31 represents the distribution of creatine concentrations in the target section P11. Accordingly this configuration is capable of presenting a result of noninvasive and accurate evaluation of a testicular function for each part of a testis.

Further in the present embodiment, the evaluation image P31 represents an evaluation result of a testicular function in each of a plurality of portions P31a to P31d obtained by dividing the target section P11. Accordingly, this configuration is capable of presenting a result of noninvasive and accurate evaluation of a testicular function for each part of a testis.

Further in the present embodiment, the image information G1 includes the MRI image of the organism P as the sectional image P1. The concentration information G2 includes information on the CEST-MRI image P2 relating to creatine of the organism P as information representing a creatine concentration in the interested section. Accordingly, this configuration can facilitate obtainment of the image information G1 and the concentration information G2.

Further in the present embodiment, the obtainment processing S1 includes the first processing S11, the second processing S12, and the third processing S13. The first processing S11 obtains a plurality of MRI P1 images an interested section of each of which is perpendicular to a predetermined direction, from the organism P. The second processing determines a main MRI image P1 which is the largest in an area of the target section P11 among the plurality of MRI images P1. The third processing obtains the CEST-MRI image P2 about the interested section of the main MRI image P1. The image information G1 includes information on the main MRI image P1. The concentration information G2 includes information on the CEST-MRI image P2 corresponding to the main MRI image P1. Accordingly, this configuration can shorten time necessary for obtaining the CEST-MRI image P2 showing a large testis.

Further in the present embodiment, the predetermined direction is determined to allow the plurality of MRI images P1 includes an MRI image P1 with a largest sectional area of the testis. Accordingly, this configuration can maximize the size of the testis shown in the CEST-MRI image P2.

Further in the present embodiment, the third processing S13 obtains a CEST-MRI image P2 about an interested section represented by at least one of auxiliary MRI images P1 prior and subsequent to the main MRI image P1 among the plurality of MRI image P1 in the predetermined direction. The concentration information G2 further includes information on a CEST-MRI image P2 corresponding to the at least one of auxiliary MRI images P1. The evaluation processing S2 generates the evaluation image P31 based on information on a CEST-MRI image P2 which is the highest in a representative value of the creatine concentration among information on CEST-MRI images P2 included in the concentration information G2. Accordingly, this configuration can improve accuracy of the result of evaluation of the testicular function.

Further in the present embodiment, the first processing S11 and the third processing S13 use the same MRI apparatus. Accordingly, this configuration does not require movement of the organism P and thus can facilitate determining a locational relationship between the MRI image P1 and the CEST-MRI image P2.

In the present embodiment, the evaluation system 1 includes the arithmetic circuit 13. The arithmetic circuit 13 is configured to perform the obtainment processing S1, the evaluation processing S2, and the presentation processing S3. The obtainment processing S1 obtains obtaining the image information G1 on the sectional image P1 representing the interested section of the organism P including the target section P11 of the testis of the organism P generated by use of magnetic resonance of hydrogen atoms, and the concentration information G2 on the creatine concentration in the interested section measured by use of magnetic resonance based on chemical exchange saturation transfer. The evaluation processing S2 generates the evaluation image P31 representing the distribution of the evaluation results of the testicular function in the target section P11 based on the concentration information G2. The presentation processing S3 presents the sectional image and the evaluation image P31. Accordingly, this configuration is capable of presenting a result of noninvasive and accurate evaluation of a testicular function for each part of a testis.

The evaluation system 1 is realized by use of the arithmetic circuit 13. This means that a method performed by the evaluation system 1 (the evaluation method) can be implemented by the arithmetic circuit 13 performing a program. This program is a computer program for performing the aforementioned evaluation method by the arithmetic circuit 13. Accordingly, this configuration is capable of presenting a result of noninvasive and accurate evaluation of a testicular function for each part of a testis.

(Variations)

Embodiments of the present disclosure are not limited to the above embodiment. The above embodiment may be modified in various ways in accordance with designs or the like to an extent that they can achieve the problem of the present disclosure. Hereinafter, some variations or modifications of the above embodiment will be listed. One or more of the variations or modifications described below may apply in combination with one or more of the others.

In one variation, it is not always necessary for the evaluation system 1 to include the measurement system 20 and the presentation system 30. In other words, it is sufficient that the evaluation system 1 includes the processing system 10. The measurement system and the presentation system 30 may be prepared as separate systems from the evaluation system 1. The processing system 10 may be implanted by not a single computer system but multiple computer systems such as multiple servers. In other words, it is not always necessary that multiple functions (components) in the evaluation system are accommodated in a single housing or casing. The multiple components of the evaluation system 1 may be distributed to multiple housing or casing. Further, at least one of functions of the evaluation system 1, for example, one of function of the arithmetic circuit 13 may be implemented by a cloud (cloud computing).

In one variation, it is not always necessary for the obtainment processing S1 to obtain the image information G1 and the concentration information G2 by directly using the measurement system 20. The obtainment processing S1 may obtain the image information G1 and the concentration information G2 from a database storing pieces of the image information G1 and the concentration information G2 prepared by use of the measurement system 20 in advance.

In one variation, it is not always necessary for the presentation processing S3 to present the synthesized image P3 resulting from replacement of an image corresponding to the target section P11 in the sectional image P1 with the evaluation image P31. The presentation processing S3 may merely present the sectional image P1 and the evaluation image P31. For example, the presentation processing S3 may present the sectional image P1 and the evaluation image P31 with they being arranged side by side. Since it is confirmed that higher the creatine concentration higher the testicular function of the organism P, the presentation processing S3 may utilize the concentration image P2 as the evaluation image P31.

In one variation, the evaluation image P31 may represent a distribution of creatine concentrations in the target section P11. In this configuration, pixel values of the evaluation image P31 may indicate creatine concentrations as such, or values or colors corresponding to classifications of creatine concentrations.

In one variation, the evaluation image P31 may represent an evaluation result of the testicular function for each of the plurality of portions P31a to P31d obtained by dividing the target section P11. The evaluation result of the testicular function may be represented by various presentation methods such as colors, mathematical figures, characters, or the like. The number of the plurality of portions P31a to P31d is not limited to a particular number but may be two or more. How to divide the target section P11 is not limited particularly.

In one variation, in the image information G1, the sectional image P1 may not be limited to MRI images of the organism P, but may be synthesized from results obtained by MRS for multiple regions of the interested section. In one variation, in the concentration information G2, the concentration image P2 may not be limited to CEST-MRI images regarding creatine of the organism P, but may be synthesized from results obtained by MRS regarding creatine for multiple regions of the interested section.

In one variation, in the obtainment processing S1, the first processing S11 may obtain a single MRI image. This means it is not always necessary for the first processing S11 to obtain multiple MRI images. In this configuration, the second processing S12 is optional and the concentration information G2 may include information on a single CEST-MRI image only. In one variation, it is not necessary for the first processing S11 and the third processing S13 to use the same MRI apparatus and they may use different MRI apparatuses.

(Aspects)

As apparent from the above embodiment and variations, the present disclosure includes the following aspects. Hereinafter, reference signs in parenthesis are attached for the purpose of clearly showing correspondence with the embodiments only.

A first aspect is an evaluation method performed by an arithmetic circuit (13). The evaluation method includes: obtainment processing (S1); evaluation processing (S2); and presentation processing (S3). The obtainment processing (S1) obtains image information (G1) on a sectional image (P1) representing an interested section of an organism (P) including a target section (P11) of a testis of the organism (P) generated by use of magnetic resonance of hydrogen atoms, and concentration information (G2) on a creatine concentration in the interested section measured by use of magnetic resonance based on chemical exchange saturation transfer. The evaluation processing (S2) generates an evaluation image (P31) representing a distribution of evaluation results of a testicular function in the target section (P11) based on the concentration information (G2). The presentation processing (S3) presents the sectional image (P1) and the evaluation image (P31). Accordingly, this aspect is capable of presenting a result of noninvasive and accurate evaluation of a testicular function for each part of a testis.

A second aspect is an evaluation method based on the first aspect. In the second aspect, the presentation processing (S3) presents the sectional image (P1) and the evaluation image (P31) by presenting a synthesized image (P3) resulting from replacement of an image corresponding to the target section (P11) in the sectional image (P1) with the evaluation image (P31). Accordingly, this aspect can present a relation between a location of the testis in the sectional image P1 and a distribution of evaluation results of the testicular function represented by the evaluation image P31 in an easy-to-understand way.

A third aspect is an evaluation method based on the second aspect. In the third aspect, the evaluation image (P31) represents a distribution of creatine concentrations in the target section (P11). Accordingly, this aspect is capable of presenting a result of noninvasive and accurate evaluation of a testicular function for each part of a testis.

A fourth aspect is an evaluation method based on the second aspect. In the fourth aspect, the evaluation image (P31) represents an evaluation result of a testicular function in each of a plurality of portions (P31a to P31d) obtained by dividing the target section (P11). Accordingly, this aspect is capable of presenting a result of noninvasive and accurate evaluation of a testicular function for each part of a testis.

A fifth aspect is an evaluation method based on any one of the first to fourth aspects. In the fifth aspect, the image information (G1) includes an MRI image of the organism (P) as the sectional image (P1). The concentration information (G2) includes information on a CEST-MRI image (P2) relating to creatine of the organism (P) as information representing a creatine concentration in the interested section. Accordingly, this aspect can facilitate obtainment of the image information (G1) and the concentration information (G2).

A sixth aspect is an evaluation method based on the fifth aspect. In the sixth aspect, the obtainment processing (S1) includes first processing (S11), second processing (S12) and third processing (S13). The first processing (S11) obtains a plurality of MRI images (P1) an interested section of each of which is perpendicular to a predetermined direction, from the organism (P). The second processing (S12) determines a main MRI image (P1) which is the largest in an area of the target section (P11) among the plurality of MRI images (P1). The third processing (S13) obtains a CEST-MRI image (P2) about an interested section of the main MRI image (P1). The image information (G1) includes information on the main MRI image (P1). The concentration information (G2) includes information on a CEST-MRI image (P2) corresponding to the main MRI image (P1). Accordingly, this aspect can shorten time necessary for obtaining the CEST-MRI image (P2) showing a large testis.

A seventh aspect is an evaluation method based on the sixth aspect. In the seventh aspect, the predetermined direction is determined to allow the plurality of MRI images (P1) includes an MRI image (P1) with a largest sectional area of the testis. Accordingly, this aspect can maximize the size of the testis shown in the CEST-MRI image (P2).

An eighth aspect is an evaluation method based on the sixth or seventh aspect. In the eighth aspect, the third processing (S13) obtains a CEST-MRI image (P2) about an interested section represented by at least one of auxiliary MRI images (P1) prior and subsequent to the main MRI image (P1) among the plurality of MRI image (P1) in the predetermined direction. The concentration information (G2) further includes information on a CEST-MRI image (P2) corresponding to the at least one of auxiliary MRI images (P1). The evaluation processing (S2) generates the evaluation image (P31) based on information on a CEST-MRI image (P2) which is the highest in a representative value of the creatine concentration among information on CEST-MRI images (P2) included in the concentration information (G2). Accordingly, this aspect can improve accuracy of the result of evaluation of the testicular function.

A ninth aspect is an evaluation method based on the eighth aspect. In the ninth aspect, the representative value is an average value, a maximum value, or a mode value. Accordingly, this aspect can improve accuracy of the result of evaluation of the testicular function.

A tenth aspect is an evaluation method based on any one of the sixth to ninth aspects. In the tenth aspect, the first processing (S11) and the third processing (S13) use the same MRI apparatus. Accordingly, this aspect does not require movement of the organism (P) and thus can facilitate determining a locational relationship between the MRI image (P1) and the CEST-MRI image (P2).

An eleventh aspect is a program for performing an evaluation method of any one of the first to tenth aspects by the arithmetic circuit (13). Accordingly, this aspect is capable of presenting a result of noninvasive and accurate evaluation of a testicular function for each part of a testis.

A twelfth aspect is an evaluation system (1) including an arithmetic circuit (13). The arithmetic circuit (13) is configured to perform: obtainment processing (S1); evaluation processing (S2); and presentation processing (S3). The obtainment processing (S1) obtains image information (G1) on a sectional image (P1) representing an interested section of an organism (P) including a target section (P11) of a testis of the organism (P) generated by use of magnetic resonance of hydrogen atoms, and concentration information (G2) on a creatine concentration in the interested section measured by use of magnetic resonance based on chemical exchange saturation transfer. The evaluation processing (S2) generates an evaluation image (P31) representing a distribution of evaluation results of a testicular function in the target section (P11) based on the concentration information (G2). The presentation processing (S3) presents the sectional image (P1) and the evaluation image (P31). Accordingly, this aspect is capable of presenting a result of noninvasive and accurate evaluation of a testicular function for each part of a testis.

Note that, the second to tenth aspects may apply to the twelfth aspect with appropriate modifications.

Further, the present disclosure can apply to a combination of a target organ of an organism and a target molecule relating to a function of the target organ. Thus, in the present disclosure, the evaluation method is an evaluation method performed by an arithmetic circuit and may include: obtainment processing of obtaining image information on a sectional image representing an interested section of an organism including a target section of a target organ of the organism generated by use of magnetic resonance of hydrogen atoms, and concentration information on a target molecule concentration relating to a function of the target organ in the interested section measured by use of magnetic resonance based on chemical exchange saturation transfer; evaluation processing of generating an evaluation image representing a distribution of evaluation results of the function in the target section based on the concentration information; and presentation processing of presenting the sectional image and the evaluation image.

As above, as examples of techniques in the present disclosure, the embodiments are described. For this purpose, the attached drawings and the description are provided. Therefore, components described in the attached drawings and the description may include not only components necessary for solving problems but also components which are unnecessary for solving problems but useful for exemplifying the above techniques. Note that, such unnecessary components should not be considered as necessary just for the reason why such unnecessary components are described in the attached drawings and the description. Further, the embodiment described above is just prepared for exemplifying the techniques in the present disclosure and thus may be subjected to various modification, replacement, addition, omission, or the like within the scope defined by claims and those equivalent range.

INDUSTRIAL APPLICABILITY

The present disclosure is applicable to evaluation methods, programs (computer programs), and evaluation systems. In more detail, the present disclosure is applicable to an evaluation method, a program (computer program) and an evaluation system in relation to a testicular function of an organism.

REFERENCE SIGNS LIST

1 Evaluation System
13 Arithmetic Circuit
G1 Image Information
G2 Concentration Information
P Organism
P1 Section Image (MRI image, Main MRI image, Auxiliary MRI image)
P11 Target Section
P2 Concentration Image (CEST-MRI image)
P3 Synthesized Image
P31 Evaluation Image
P31a-P31d Portion
S1 Obtainment Processing
S11 First Processing
S12 Second Processing
S13 Third Processing
S2 Evaluation Processing
S3 Presenting Processing

The invention claimed is:
1. An evaluation method performed by an arithmetic circuit, comprising:
   obtaining image information on a sectional image including a target section image representing a testis of an organism, and the sectional image being generated by use of magnetic resonance of hydrogen atoms using a magnetic resonance imaging (MRI) apparatus;
   obtaining concentration information on a creatine concentration in the testis of the organism, the creatine concentration being measured by use of magnetic resonance based on chemical exchange saturation transfer (CEST) using the MRI apparatus;
   generating an evaluation image representing a distribution of evaluation results of a testicular function for each of a plurality of portions of the target section image based on the concentration information;
   generating a synthesized image by replacing (i) the target section image representing the testis of the organism in the sectional image with (ii) the evaluation image representing the distribution of evaluation results of the testicular function for each of the plurality of portions of the target section image; and
   displaying the synthesized image on a display terminal,
   wherein the obtaining the image information includes:
      obtaining a plurality of MRI images of the testis of the organism at a regular interval along a predetermined direction;

determining a first MRI image from among the plurality of MRI images, the first MRI image having a largest sectional area of the target section image from among the plurality of MRI images; and
      obtaining a first CEST-MRI image corresponding to the first MRI image,
   wherein the image information includes information on the first MRI image, and
   wherein the concentration information includes first information on the first CEST-MRI image relating to creatine of the organism as information representing the creatine concentration in the testis of the organism.
2. The evaluation method of claim 1, wherein the evaluation image represents a distribution of creatine concentrations in each of the plurality of portions of the target section image.
3. The evaluation method of claim 1, wherein the predetermined direction is determined based on a maximum sectional area of the testis of the organism.
4. The evaluation method of claim 3, further comprising:
   obtaining a second CEST-MRI image corresponding to a second MRI image from among the plurality of MRI images, the second MRI image being prior to the first MRI image in the predetermined direction; and
   obtaining a third CEST-MRI image corresponding to a third MRI image from among the plurality of MRI images, the third MRI image being subsequent to the first MRI image in the predetermined direction, wherein
   the concentration information further includes second information on the second CEST-MRI image and third information on the third CEST-MRI image, and
   the evaluation image is generated based on one of the first information on the first CEST-MRI image, the second information on the second CEST-MRI image, and the third information on the third CEST-MRI image having a highest representative value of the creatine concentration.
5. The evaluation method of claim 4, wherein the plurality of MRI images and the first CEST-MRI image are obtained using the MRI apparatus.
6. The evaluation method of claim 3, wherein the plurality of MRI images and the first CEST-MRI image are obtained using the MRI apparatus.
7. The evaluation method of claim 1, further comprising:
   obtaining a second CEST-MRI image corresponding to a second MRI image from among the plurality of MRI images, the second MRI image being prior to the first MRI image in the predetermined direction; and
   obtaining a third CEST-MRI image corresponding to a third MRI image from among the plurality of MRI images, the third MRI image being subsequent to the first MRI image in the predetermined direction, wherein
   the concentration information further includes second information on the second CEST-MRI image and third information on the third CEST-MRI image, and
   the evaluation image is generated based on one of the first information on the first CEST-MRI image, the second information on the second CEST-MRI image, and the third information on the third CEST-MRI image having a highest representative value of the creatine concentration.
8. The evaluation method of claim 7, wherein the representative value is an average value, a maximum value, or a mode value.

9. The evaluation method of claim 8, wherein
the plurality of MRI images and the first CEST-MRI
image are obtained using the MRI apparatus.

10. The evaluation method of claim 7, wherein
the plurality of MRI images and the first CEST-MRI
image are obtained using the MRI apparatus.

11. The evaluation method of claim 1, wherein
the plurality of MRI images and the first CEST-MRI
image are obtained using the MRI apparatus.

12. A non-transitory storage medium storing a program
for performing the evaluation method of claim 1 by the
arithmetic circuit.

13. An evaluation system comprising an arithmetic circuit
configured to perform:

obtaining image information on a sectional image includ-
ing a target section image representing a testis of an
organism, the sectional image being generated by use
of magnetic resonance of hydrogen atoms using a
magnetic resonance imaging (MRI) apparatus;

obtaining concentration information on a creatine con-
centration in the testis of the organism, the creatine
concentration being measured by use of magnetic reso-
nance based on chemical exchange saturation transfer
(CEST) using the MRI apparatus;

generating an evaluation image representing a distribution
of evaluation results of a testicular function for each of a plurality of portions of the target section image based
on the concentration information;

generating a synthesized image by replacing (i) the target
section image representing the testis of the organism in
the sectional image with (ii) the evaluation image
representing the distribution of evaluation results of the
testicular function for each of the plurality of portions
of the target section image; and displaying the synthesized image on a display terminal, wherein the obtaining the image information includes:

obtaining a plurality of MRI images of the testis of the
organism at a regular interval along a predetermined
direction;

determining a first MRI image from among the plural-
ity of MRI images, the first MRI image having a
largest sectional area of the target section image from
among the plurality of MRI images; and obtaining a first CEST-MRI image corresponding to the
first MRI image, wherein the image information includes information on
the first MRI image, and wherein the concentration information includes first infor-
mation on the first CEST-MRI image relating to cre-
atine of the organism as information representing the
creatine concentration in the testis of the organism.

* * * * *